US010923218B2

(12) United States Patent
Bernstein et al.

(10) Patent No.: US 10,923,218 B2
(45) Date of Patent: Feb. 16, 2021

(54) DATA SYNCHRONIZATION BETWEEN TWO OR MORE ANALYTE DETECTING DEVICES IN A DATABASE

(71) Applicant: ABBOTT DIABETES CARE INC., Alameda, CA (US)

(72) Inventors: Daniel M. Bernstein, El Granada, CA (US); Gary A. Hayter, Oakland, CA (US); Timothy C. Dunn, San Francisco, CA (US); Mani Gopal, Hillsborough, CA (US); Eric Davis, Castro Valley, CA (US); Brittany K. Bradrick, San Francisco, CA (US); Todd Winkler, Cameron Park, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 16/918,563

(22) Filed: Jul. 1, 2020

(65) Prior Publication Data
US 2020/0357492 A1 Nov. 12, 2020

Related U.S. Application Data

(63) Continuation of application No. 15/684,456, filed on Aug. 23, 2017, which is a continuation of application
(Continued)

(51) Int. Cl.
*G16H 10/60* (2018.01)
*A61B 5/00* (2006.01)
(Continued)

(52) U.S. Cl.
CPC .......... *G16H 10/60* (2018.01); *A61B 5/0022* (2013.01); *A61B 5/1172* (2013.01);
(Continued)

(58) Field of Classification Search
CPC ...... G16H 10/60; G16H 40/63; A61B 5/4839; A61B 5/14532; A61B 5/1172;
(Continued)

(56) References Cited

U.S. PATENT DOCUMENTS 4,545,382 A 10/1985 Higgins et al.
4,711,245 A 12/1987 Higgins et al.
(Continued)

FOREIGN PATENT DOCUMENTS

WO  WO  4/2012
PCT/US2011/066412

OTHER PUBLICATIONS

Barker, N., "A Practical Introduction to the Bootstrap Using the SAS System", SAS Conference Proceedings, 2005, Paper PK02, 17 pages.
(Continued)

*Primary Examiner* — Linh Giang Le
(74) *Attorney, Agent, or Firm* — One LLP

(57) ABSTRACT

An analyte measurement system includes one or more handheld analyte meters and/or measurement devices and a means for collecting data, preserving data integrity, and uniquely identifying patient data received from multiple sources. For example, provided herein is a means to uniquely identify patients and their data when the data is collected from one or more measurement devices. By providing a way to allow the patients to use multiple sources to collect data, the system described herein provides patients with more flexibility, which should encourage better compliance to protocols. Further, by having a way to uniquely identify patients' data without requiring a patient to only use one analyte meter, for example, data can be centralized and analysis can be done with more assurance that all of the patient's data is being considered in the analyses.

19 Claims, 4 Drawing Sheets

Related U.S. Application Data

No. 13/984,809, filed as application No. PCT/US2011/066422 on Dec. 21, 2011, now Pat. No. 9,760,679.

(60) Provisional application No. 61/442,063, filed on Feb. 11, 2011.

(51) Int. Cl.
  *A61B 5/1172* (2016.01)
  *A61B 5/145* (2006.01)
  *A61B 5/1473* (2006.01)
  *A61B 5/021* (2006.01)
  *A61M 5/142* (2006.01)
  *A61M 5/172* (2006.01)
  *G16H 40/63* (2018.01)

(52) U.S. Cl.
  CPC ........ *A61B 5/1473* (2013.01); *A61B 5/14532* (2013.01); *A61B 5/4839* (2013.01); *A61B 5/021* (2013.01); *A61M 5/142* (2013.01); *A61M 5/172* (2013.01); *G16H 40/63* (2018.01)

(58) Field of Classification Search
  CPC ..... A61B 5/0022; A61B 5/1473; A61B 5/021; A61M 5/172; A61M 5/142
  See application file for complete search history.

(56) References Cited

U.S. PATENT DOCUMENTS

| | | |
|---|---|---|
| 5,262,035 A | 11/1993 | Gregg et al. |
| 5,262,305 A | 11/1993 | Heller et al. |
| 5,264,104 A | 11/1993 | Gregg et al. |
| 5,320,725 A | 6/1994 | Gregg et al. |
| 5,356,249 A | 10/1994 | Heller et al. |
| 5,509,410 A | 4/1996 | Hill et al. |
| 5,536,249 A | 7/1996 | Castellano et al. |
| 5,543,236 A | 8/1996 | Heller et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 5,925,021 A | 7/1999 | Castellano et al. |
| 6,071,391 A | 6/2000 | Gotoh et al. |
| 6,103,033 A | 8/2000 | Say et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,281,006 B1 | 8/2001 | Heller et al. |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,616,819 B1 | 9/2003 | Liamos et al. |
| 6,618,934 B1 | 9/2003 | Feldman et al. |
| 6,638,716 B2 | 10/2003 | Heller et al. |
| 6,650,471 B2 | 11/2003 | Doi |
| 6,654,625 B1 | 11/2003 | Say et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,932,892 B2 | 8/2005 | Chen et al. |
| 6,932,894 B2 | 8/2005 | Mao et al. |
| 6,942,518 B2 | 9/2005 | Liamos et al. |
| 7,041,468 B2 | 5/2006 | Drucker et al. |
| 7,167,818 B2 | 1/2007 | Brown |
| 7,299,082 B2 | 11/2007 | Feldman et al. |
| 7,766,829 B2 | 8/2010 | Sloan et al. |
| 7,866,026 B1 | 1/2011 | Wang et al. |
| 8,262,874 B2 | 9/2012 | Forrow et al. |
| 8,514,086 B2 | 8/2013 | Harper et al. |
| 8,601,465 B2 | 12/2013 | Bernstein et al. |
| 9,913,599 B2 | 3/2018 | Bernstein et al. |
| 2002/0193679 A1* | 12/2002 | Malave ................ G16H 40/67 600/407 |
| 2003/0208110 A1 | 11/2003 | Mault et al. |
| 2004/0054263 A1 | 3/2004 | Moerman |
| 2004/0186365 A1 | 9/2004 | Jin et al. |
| 2004/0254434 A1 | 12/2004 | Goodnow et al. |
| 2005/0101841 A9 | 5/2005 | Kaylor et al. |
| 2005/0182306 A1 | 8/2005 | Sloan |
| 2006/0025662 A1 | 2/2006 | Buse et al. |
| 2006/0040402 A1 | 2/2006 | Brauker et al. |
| 2006/0091006 A1 | 5/2006 | Wang et al. |
| 2006/0173260 A1* | 8/2006 | Gaoni ................ G06F 19/3481 600/365 |
| 2006/0224141 A1 | 10/2006 | Rush et al. |
| 2007/0056858 A1 | 3/2007 | Chen et al. |
| 2007/0068807 A1 | 3/2007 | Feldman et al. |
| 2007/0095661 A1 | 5/2007 | Wang et al. |
| 2007/0100222 A1* | 5/2007 | Mastrototaro ......... G06Q 50/22 600/365 |
| 2007/0108048 A1 | 5/2007 | Wang et al. |
| 2007/0199818 A1 | 8/2007 | Petyt et al. |
| 2007/0227911 A1 | 10/2007 | Wang et al. |
| 2007/0233013 A1 | 10/2007 | Schoenberg |
| 2008/0066305 A1 | 3/2008 | Wang et al. |
| 2008/0076969 A1* | 3/2008 | Kraft .................... G06F 19/3418 600/300 |
| 2008/0081977 A1 | 4/2008 | Hayter et al. |
| 2008/0102441 A1 | 5/2008 | Chen et al. |
| 2008/0119705 A1 | 5/2008 | Patel et al. |
| 2008/0148873 A1 | 6/2008 | Wang |
| 2008/0161666 A1 | 7/2008 | Feldman et al. |
| 2008/0234992 A1 | 9/2008 | Ray et al. |
| 2008/0249470 A1 | 10/2008 | Malave et al. |
| 2008/0267823 A1 | 10/2008 | Wang et al. |
| 2009/0054748 A1 | 2/2009 | Feldman |
| 2009/0095625 A1 | 4/2009 | Forrow |
| 2009/0164251 A1 | 6/2009 | Hayter |
| 2009/0171589 A1 | 7/2009 | Kovatchev |
| 2009/0240128 A1 | 9/2009 | Mensinger et al. |
| 2009/0247857 A1 | 10/2009 | Harper et al. |
| 2009/0253970 A1 | 10/2009 | Bashan et al. |
| 2009/0255811 A1 | 10/2009 | Forrow et al. |
| 2009/0294277 A1 | 12/2009 | Thomas et al. |
| 2010/0081909 A1 | 4/2010 | Budiman et al. |
| 2010/0198034 A1 | 8/2010 | Thomas et al. |
| 2010/0198142 A1* | 8/2010 | Sloan ................ A61B 5/14532 604/66 |
| 2010/0213057 A1 | 8/2010 | Feldman et al. |
| 2010/0222648 A1 | 9/2010 | Tan |
| 2010/0230285 A1 | 9/2010 | Hoss et al. |
| 2010/0256047 A1 | 10/2010 | Sieh et al. |
| 2010/0274592 A1 | 10/2010 | Nitzan et al. |
| 2010/0312577 A1 | 12/2010 | Goodnow et al. |

(56) References Cited

U.S. PATENT DOCUMENTS

| | | |
|---|---|---|
| 2010/0313105 A1 | 12/2010 | Nekoomaram et al. |
| 2010/0324392 A1 | 12/2010 | Yee et al. |
| 2010/0325868 A1 | 12/2010 | Wang et al. |
| 2010/0326842 A1 | 12/2010 | Mazza et al. |
| 2011/0015511 A1 | 1/2011 | Bousamra et al. |
| 2011/0021889 A1 | 1/2011 | Hoss et al. |
| 2011/0082484 A1 | 4/2011 | Saravia et al. |
| 2011/0098548 A1 | 4/2011 | Budiman et al. |
| 2011/0106126 A1 | 5/2011 | Love et al. |
| 2011/0119080 A1 | 5/2011 | Hayter et al. |
| 2011/0125530 A1 | 5/2011 | Drucker et al. |
| 2011/0160544 A1 | 6/2011 | Hayter |
| 2011/0184264 A1 | 7/2011 | Galasso et al. |
| 2011/0190603 A1 | 8/2011 | Stafford |
| 2011/0191044 A1 | 8/2011 | Stafford |
| 2011/0213225 A1 | 9/2011 | Bernstein et al. |
| 2011/0256024 A1 | 10/2011 | Cole et al. |
| 2011/0319729 A1 | 12/2011 | Donnay et al. |
| 2012/0157801 A1 | 6/2012 | Hoss et al. |
| 2014/0088392 A1 | 3/2014 | Bernstein et al. |
| 2014/0142981 A1 | 5/2014 | Gopal et al. |

OTHER PUBLICATIONS

Benton, D., et al., "Performance of the Parametric Bootstrap Method in Small Sample Interval Estimates", Adv. & Appl. in Stat., 2002, vol. 2, No. 3, pp. 269-285.

Nathan, D. M., et al., "Translating the A1C Assay Into Estimated Average Glucose Values", Diabetes Care, 2008, vol. 31, No. 8, pp. 1473-1478.

The Diabetes Control and Complications Trial Research Group, "The Effect of Intensive Treatment of Diabetes on the Development and Progression of Long-Term Complications in Insulin-Dependent Diabetes Mellitus", The New England Journal od Medicine, 1993, vol. 329, No. 14, pp. 977-986.

* cited by examiner

DATA SYNCHRONIZATION BETWEEN TWO OR MORE ANALYTE DETECTING DEVICES IN A DATABASE

CROSS-REFERENCE TO RELATED APPLICATIONS

This application is a continuation of U.S. application Ser. No. 15/684,456, filed Aug. 23, 2017, which is a continuation of U.S. application Ser. No. 13/984,809, filed Nov. 20, 2013, now U.S. Pat. No. 9,760,679, which is a national phase application of PCT Application No. PCT/US11/66422, filed Dec. 21, 2011, which claims the benefit of U.S. Provisional Application No. 61/442,063, filed Feb. 11, 2011, all of which are incorporated by reference herein in their entireties and for all purposes.

This application is related to U.S. Provisional Patent Application No. 61/442,085 filed on Feb. 11, 2011; U.S. Provisional Application No. 61/486,117 filed on May 13, 2011; U.S. Provisional Patent Application No. 61/442,092 filed on Feb. 11, 2011; U.S. Provisional Application No. 61/485,840 filed on May 13, 2011; U.S. Provisional Application No. 61/442,093 filed on Feb. 11, 2011, and U.S. Provisional Application No. 61/442,097 filed on Feb. 11, 2011, all of which are incorporated by reference herein in their entireties and for all purposes.

BACKGROUND OF THE INVENTION

The Field of the Invention

The present invention relates to analyte measurement systems. More specifically, the present invention relates to a means for preserving data integrity and uniquely identifying patient data received from multiple sources.

Background

One tool used in diabetes management is an analyte meter. An analyte meter is typically used to measure the blood glucose level of a user based on a sample of blood. The process of using an analyte meter is not complicated, and is often performed several times a day. First, the user inserts an analyte test strip into a test strip port of the meter. The user then lances her finger to obtain a small sample of blood. The blood sample is then placed onto the analyte test strip, and the meter analyzes the blood sample. The meter then typically displays a blood glucose level from the analysis.

In today's budget conscious health care world there is intense pressure to deliver improved outcomes in cost conscious ways. One way to accomplish this goal in the realm of diabetes care is to more effectively use blood glucose (BG) data and other biometric data collected from patients to make effective therapy and lifestyle suggestions. To effectively collect and analyze data, the patient must comply with prescribed BG (or other biometric) testing protocols. There is also a need for providing a means for easily collecting and communicating data.

What is needed is a means for collecting data, preserving data integrity, and uniquely identifying patient data received from multiple sources.

BRIEF SUMMARY

Presented herein is an analyte measurement system. The analyte measurement system includes one or more handheld analyte meters and/or measurement devices and a means for collecting data, preserving data integrity, and uniquely identifying patient data received from multiple sources. For example, provided herein is a means to uniquely identify patients and their data when the data is collected from one or more measurement devices. By providing a way to allow the patients to use multiple sources to collect data, the system described herein provides patients with more flexibility, which should encourage better compliance to protocols. Further, by having a way to uniquely identify patients' data without requiring a patient to only use one analyte meter, for example, data can be centralized and analysis can be done with more assurance that all of the patient's data is being considered in the analyses.

In addition, the methods discussed herein consider ease-of-use. By providing easy to use systems, patients are more likely to comply with testing protocols.

Finally, these methods also keep in mind data integrity. When multiple meters are used, the likelihood of a meter being lost or stolen increases. The systems proposed allow patients to maintain multiple meters without excessive risk to patient privacy as it relates to medical data (i.e.; HIPAA requirements). The methods guarantee that the data coming from any particular meter is from the patient the meter was assigned to, and therefore protects the patient's privacy.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the present invention.

DETAILED DESCRIPTION OF THE INVENTION

Before the embodiments of the present invention are described, it is to be understood that this invention is not limited to particular embodiments described, and as such may, of course, vary. It is also to be understood that the terminology used herein is for the purpose of describing particular embodiments only, and is not intended to be limiting, since the scope of the embodiments of the invention will be limited only by the appended claims.

Figure 1:
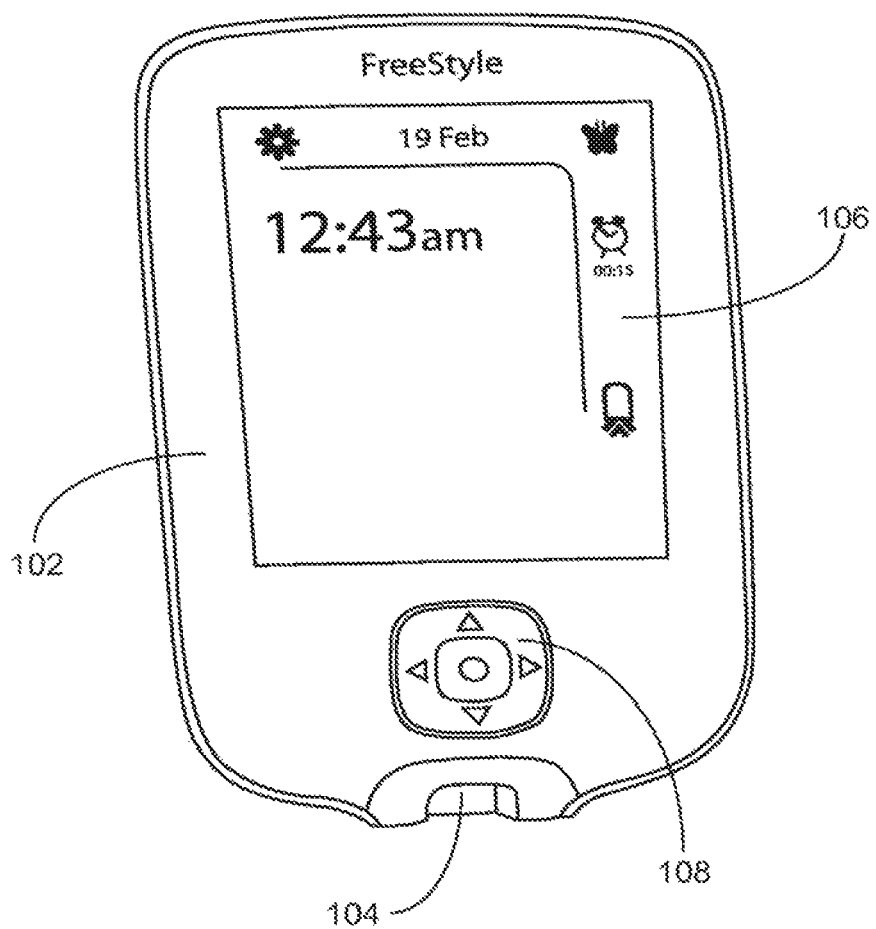
FIG. 1 provides a front-side view of handheld analyte measurement device in accordance with one embodiment presented herein.

FIG. 1 provides a front-side view of handheld analyte measurement device, such as an analyte meter 102, in accordance with one embodiment presented herein. In one embodiment, analyte meter 102 includes a test strip port 104, a display unit 106, and at least one control button 108. In practice, an analyte test strip (or sensor) is inserted into test strip port 104 in order to conduct an analyte test; for example, a blood glucose reading or a blood ketone reading. Meter 102 includes software (as described below) to analyze the sample placed on the test strip, and the results of the analysis are typically displayed to the user via display unit 106. The user may also use control button 108 to provide appropriate instructions to meter 102.

In one embodiment, meter 102 includes one or more diabetes management software applications. The integration of software applications with meter 102 provides an opportunity to augment traditional glucose and/or ketone readings to provide more useful information and feedback to patients and doctors. As such, meter 102, with loaded software applications, can be part of a robust therapy management system. The software applications can be factory pre-loaded, or installed by the user or health care provider after first use by the user.

Analyte meter 102 may further include one or more internal or external communication modules. The communication module(s) may be used to receive and/or transmit data and/or program instructions. The communication module(s) may also download software applications from one or more servers. In one embodiment, the communication module is used to communicate with one or more external devices; such as, for example, a central server or central database, a medication (drug) deliver device; a cellular phone; a laptop computer; a mobile device, such as a PDA, iPhone, iPad, tablet computer, etc.; a desktop computer; an analyte meter; and/or another analyte measurement system. In one embodiment, the communication module can be configured for wireless communication to an external device. Wireless communication may be provided by, for example, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

The methods described in this disclosure depend on the collection of identifying information by a central database, server(s), or "cloud." For the scenarios provided below, the following are assumed: 1) a centralized server or database exists that can be accessed by the user through multiple conduits (e.g., a web-based database accessible from any internet enabled PC, cell phone, tablet PC, etc.); 2) the analyte meter contains a unique identifier (e.g., serial number); and 3) the conduits used to upload data from the analyte meter to the central database are uniquely identifiable (e.g., via a MAC address or calling phone number). The following scenarios are considered below: 1) the patient has multiple analyte meters in multiple locations (e.g., at home, office, gym, etc.); 2) the patient's BG readings are sometimes taken at a hospital or clinic, where there is sanctioned use of the meters by multiple patients; 3) the patient is given multiple meters that are re-used by the clinic, to take home; 4) multiple patients share a single meter (e.g., a husband borrows wife's meter); and 5) a meter is lost or stolen and an attempt to use the meter is made by an unauthorized user.

As used herein, the term "device" is intended to include multiple analyte meters (either discreet or continuous blood glucose meters), wired- or wireless-equipped biometric measurement devices (e.g., blood pressure measurement devices), or any other medical devices. In some cases, the device may act as a data hub such that it contains not just glucose measurement data, but also other biometric data (e.g., blood pressure data, weight, pulse rate, etc.) that has been manually or automatically entered into the device or communicated to the device. The methods described herein provides a way to uniquely identify the patient regardless of which device is used and to associate the uploaded data with that patient. The following section describes the various ways in which this unique identification can be done.

1) Barcode, RFID, or Fingerprint Method.

In one embodiment, the device may include a fingerprint reader to identify the patient. In another embodiment, the device may include a barcode or other optical reader that identifies the patient via a handheld identifier tag. In another embodiment, the device may include an RFID reader that identifies the patient via a RF card/tag kept by the patient. Identifiers or RF cards/tags may be made small enough to fit on a key chain, in a wallet, or in a carrying case that contains the patient's device, lancets, and/or test strips. In one embodiment, the patient is not allowed to take an analyte reading without first making contact (physical or electrical) between the device and identifier (or taking a fingerprint reading). The identifier used at the time of the analyte reading may be attached to each said reading. Thus each reading uniquely identifies itself to the patient. As long as the patient only uses devices that require the identifier, all of their data will be uniquely identifiable and can be aggregated to a central location. Devices may be programmed to accept only one single identifier (or fingerprint), to enforce no sharing of the device, or multiple identifiers to allow sanctioned re-use of devices. In the case where only a single identifier is allowed, the device will have to be paired with the identifier on first use.

2) Association of Devices and Conduit Devices with a Patient.

Figure 2:
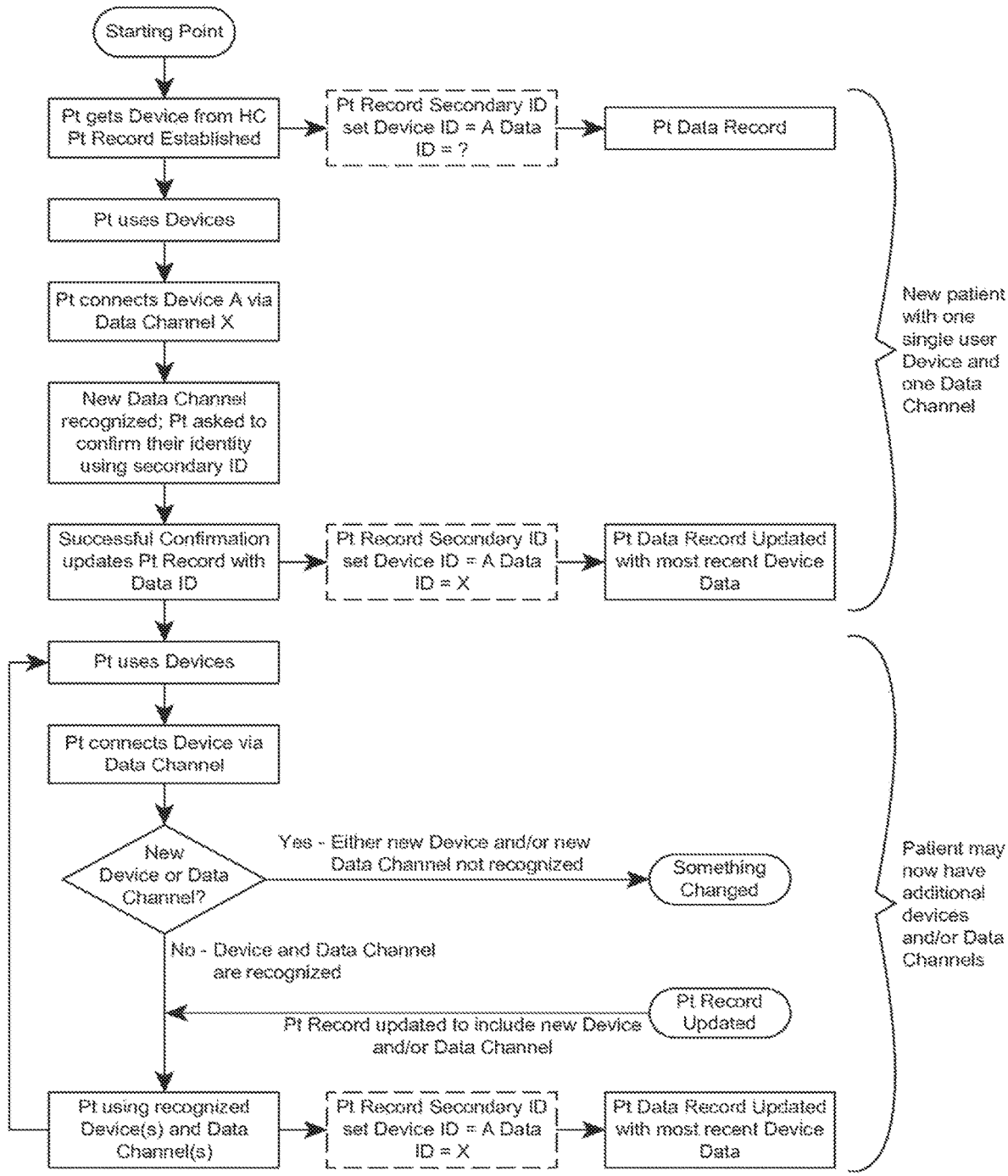
FIG. 2 is a flowchart illustrating one embodiment presented herein.
Figure 3:
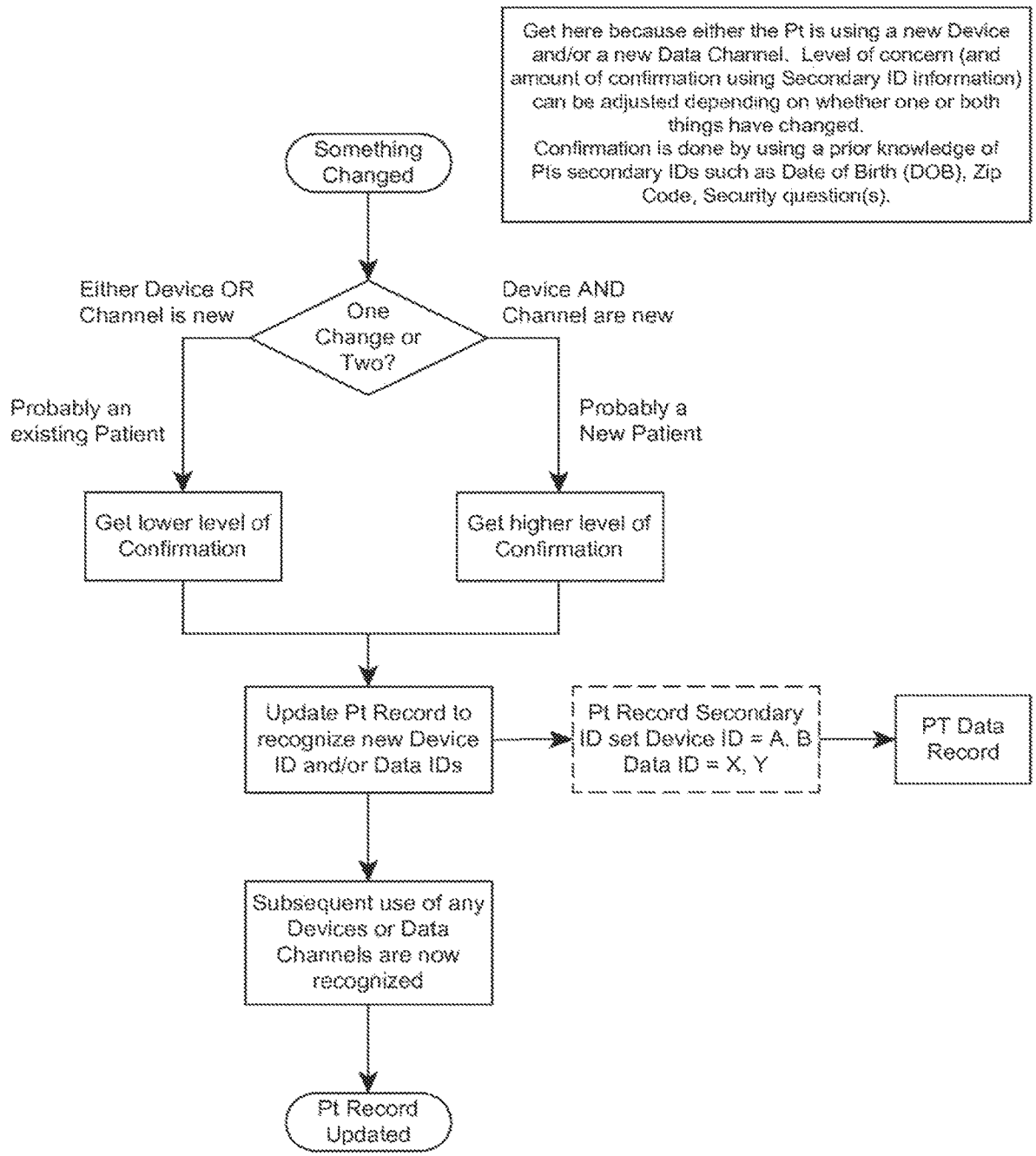
FIG. 3 is a continuation of the flowchart from FIG. 2.

The first time a patient uploads data, either directly to a PC or cellphone, or to the internet via a PC or cellphone conduit, the identifiers (MAC addresses, serial numbers, etc.) of the device and data conduit are collected. At the time a patient is registered, a Patient Record is established in the database system and the Patient Record includes "Secondary ID information" (that may be used to confirm a patient's identity without communicating their full name). This Secondary ID Information includes information such as SSN, DOB, zip code, mother's maiden name, etc. A patient may also be assigned a unique identifier (and optionally a password) at the time of registration. The next time the aggregating database sees the same analyte device or conduit it may assume that it is the same patient "returning" with more data (or may provide a verification prompt). When the aggregating system does not recognize the device and/or conduit devices, it can ask if the patient is a returning patient (or simply ask the patient to identify themselves using Secondary Information (to minimize patient privacy issues). If the patient is a returning patient, they could be asked for their unique ID and password, and/or other Secondary ID Information or identifiers to confirm their identity. An unrecognized patient would have to be registered in the system before they could access the system. Once the patient identity has been confirmed, the new device and/or data conduit identifiers can be added to their record. This scenario is illustrated in the flowchart in FIGS. 2 and 3.

Another aspect of this invention is that a unique patient ID, generated by the central database, can be stored in the device software and in communication software in the conduit as part of the registration process—this communication software can be loaded into the conduit by the device the first time it is attached or loaded from the web or other communication network at an address specified by the device. This way the unique patient ID format can be controlled by the central database and uniqueness can be guaranteed. When the data is uploaded, the unique patient ID is included twice in the upload stream, by the device software and by software in the conduit (communication driver), and extracted by the central database for data association. When the unique patient ID from the device is not recognized, or that from the conduit are not recognized, the new device or conduit proceeds to a registration protocol, as described above. Other means to perform this function can be contemplated, such as having the conduit software check the device for matching patient IDs and sending a flag to the central database if they do not match.

For multiple patients using the same conduit, the communication driver would need to maintain multiple unique patient IDs and some additional patient information (such as first name), including security information such as a password, to deal with the situation where new devices are introduced. When a new device is detected and multiple unique patient IDs are stored in the communication driver, it would need to request the user to select from the list patient information associated with the stored unique patient IDs.

Process flows are provided below—these are in terms of a device attached via wire to a PC connected to the internet; however, the general method is similar for other connection methods such as 3G cellular connection, or pager network based communication.

An example registration process flow is as follows: a) register unique patient ID on website—patient provides additional security information; b) Connect new device to new PC—device installs communication driver on PC (communication driver has instructions to upload data from device to web address automatically when device is attached); and c) upon completion of the registration process, website downloads unique patient ID to device and communication driver.

An example upload process flow is as follows: a) attach device to PC, upload begins automatically as driven by communication driver; b) device and communication driver both place unique patient ID in data stream; and c) central database recognizes and matches both unique patient IDs and stores data associated with this ID.

An example upload process flow where a new device is introduced is as follows: a) attach new device to PC with existing communication driver; b) device places a null character in the unique patient ID field of the data stream; c) the communication driver detects the mismatch of the unique patient ID with any of its stored IDs and requests the user to identify the unique patient ID based on associated patient information and/or security information; d) upon proper confirmation, the communication driver downloads the unique patient ID to the new device and includes the unique patient ID in the device field of the data stream sent to the central database; and e) central database recognizes and matches both unique patient IDs and stores data associated with this ID. For configurations where the upload conduit may not have a user interface, the security confirmation could be provided through the device UI.

An example upload process flow where a new PC is introduced is as follows: a) attach device to a new PC—device installs communication driver on PC (communication driver has instructions to upload data from device to web address automatically when device is attached); b) device loads unique patient ID into communication driver; c) device and communication driver both place unique patient ID in data stream; and d) central database recognizes and matches both unique patient IDs and stores data associated with this ID.

3) Shared Device in the Context where Patient May have Multiple Analyte Devices.

Figure 4:
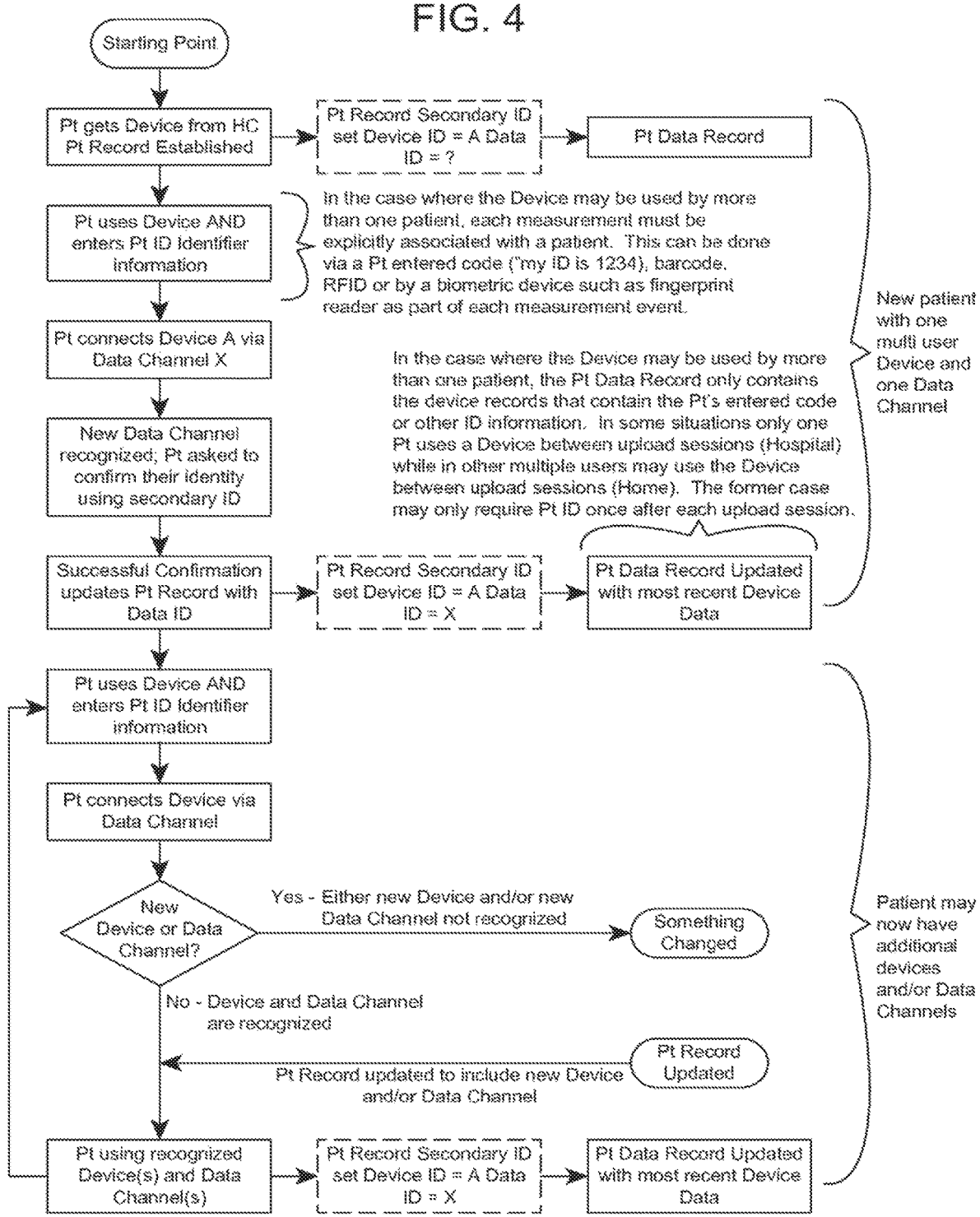
FIG. 4 is a flowchart illustrating another embodiment presented herein.

This scenario expands on the case above. This scenario adds in the case where a patient uses a device that other patients may also use between upload operations (i.e., the analyte data in the device may come from more than one patient with each upload cycle). This scenario could occur in a home setting for example where a device may be shared by several people. In this case, it is necessary for the system to have positive knowledge of the source of each analyte measurement. The flowchart in FIG. 4 provides a method in accordance with such an embodiment.

4) Patient Information Entered into the Device.

This scenario envisions the hospital setting where devices may be used for multiple patients sequentially, but not concurrently. Whenever a new patient will be using a device, information identifying the patient can be entered into the device and associated with the data when it is sent to the aggregating device. Patient data need only be entered once until the device is given to a new patient.

5) Shared Device with Self-Modifying Serial Number.

This scenario envisions a device given to a patient in a clinic in order to take home. The device may not be as sophisticated as a hospital device and therefore there may not be a way for the patient to enter any identifying information. Whenever the device is given to a new patient, a monotonically increasing identifier is added to the devices log. This can be made to happen at the clinic by having a function built into the device for initializing a new patient. This function increments the identifier and puts it in the log. Subsequently each record in the log is identified by the device's serial number, monotonically increasing identifier, and record ID. The monotonically increasing identifier can be said to be part of the device's serial number, so each time the aggregating database sees a new device serial number, it knows to ask if this is a new patient. It is assumed that the aggregating database software is running on a platform that can more easily handle user input, such as a cell phone, tablet, or PC.

6) Lost or Stolen Device.

The analyte device may be lost or stolen. In order to guarantee data integrity, it is important that data entered by an unauthorized user not get assigned to the patient to whom the device was assigned, nor can the unauthorized user view the original patient's data. When the unauthorized user tries to upload the data to the central database, the database will detect that the conduit (PC, cellphone, tablet, etc.) is different than what was used by that patient before. The database software determines this because it has linked device ID, conduit, and patient data in its database. The database software will issue a pre-arranged challenge question to the user (e.g., What is your mother's maiden name?). If the challenge is answered successfully, the database accepts the data from the device, otherwise the data from that device is rejected and viewing of previous data is blocked. Furthermore, the system can be configured to only allow uploading when the device is connected to a limited set of data conduits.

Another aspect of this invention provides for synchronization of data between devices. For instance, if a patient utilized two different devices, it would be useful to have the data from one device additionally stored on the other. As such, when the patient examines their data on one device, they may get a complete picture of their analyte measurements. Another example is a patient who has a device and a cellphone that accepts manual analyte reading entries (presumably from a separate device). The two devices could synchronize using well established synchronization techniques (common with PDAs). They could synchronize periodically over a wireless channel such as Bluetooth. They could synchronize when connected via a wired channel. A preferred method is that they could synchronize during upload of data to a central database. The central database would be aware of multiple devices of compatible data-types and would perform a difference of its stored data (after upload) from predefined period of time and download the difference to the device to be stored. Variations of this synchronization scheme can be contemplated.

Another aspect of this invention deals with the possibility that identical data may come through different conduits—such as a device that can upload both through a PC and through a cellular channel. To mitigate "double counting" of readings, additional data of a particular data-type would be ignored (that is, not stored) by the central database if data of that data-type already existed with the exact same timestamp. Alternatively, the data in this situation may be stored but flagged as duplicate. As such, data processing (or preprocessing) routines would need to take the flagged duplicate data into account as needed.

Though this invention description may focus on blood glucose devices, the techniques described apply to all devices that may be used to upload patient analyte data or other patient data to a central database, such as cell phones, tablet PC's, a dedicated communication router (e.g., via Bluetooth from the device and via cellular to the internet), etc., where the data may be aggregated with these devices from manual input, and/or wired or wireless communication from a measurement device or other intermediate storage devices. This invention can also apply to any device used to measure patient data, such as continuous glucose (CG) devices, blood pressure (BP) measurement devices, heightscales, and the like.

In another embodiment, there is provided mechanisms to enforce system configuration requirements. Electronic system update configuration requirements can be enforced using key codes that are incorporated in the communication messages sent between system components. Key codes are primarily available for access by a PC (or any other electronic device). The codes may be used as a convenient book keeping tool to manage which version of the device may function with a specific version of a PC application using a particular serial command. For instance, a serial command may include a two byte key code where in the original system the PC application will issue a value of code=00 when it sends the command to a device. The original version of the device can be designed with a serial command function that will accept commands with code with a range of 00 to 0F. In this way, if another version of the device has an updated serial command that allows a code range of 00 to 1F, then the original PC application version will still work with this updated device, along with newer versions of the PC application that have codes in this range (in regards specifically to this particular serial command). If an updated PC application is not intended to work with the first device version but only the second device version, then the code for the PC application should be set between 10 to 1F. If the updated device is not intended to work with the original PC application, then the code for the device could be set to 10 to 1F.

Another application for the key code mechanism has a key code included in the pairing message exchange between the device and a drug delivery device, in the same fashion as described above for device serial commands access primarily by PC applications. Here the unique feature is that the key code only needs to be included in a pairing message in order to enforce all communication restrictions between versions of device and the drug delivery device, since they may not communicate (other than for pairing attempts) unless they are paired. This allows full control over which device versions will work with which drug delivery device versions.

The same effect could be used by just changing the command name or format. For instance, a device could be designed to accept serial commands with names $acona, $aconb, and $aconx, and the PC application could issue $aconb. Also, the device could be designed to accept a serial command with three parameters and with five parameters. However, the key code technique is much more convenient and easier to manage.

Integration with Medication Delivery Devices and/or Systems

In some embodiments, the analyte measurement systems disclosed herein may be included in and/or integrated with, a medication delivery device and/or system, e.g., an insulin pump module, such as an insulin pump or controller module thereof, or insulin injection pen. In some embodiments the analyte measurement system is physically integrated into a medication delivery device. In other embodiments, an analyte measurement system as described herein may be configured to communicate with a medication delivery device or another component of a medication delivery system. Additional information regarding medication delivery devices and/or systems, such as, for example, integrated systems, is provided in U.S. Patent Application Publication No. US2006/0224141, published on Oct. 5, 2006, entitled "Method and System for Providing Integrated Medication Infusion and Analyte Monitoring System," and U.S. Patent Application Publication No. US2004/0254434, published on Dec. 16, 2004, entitled "Glucose Measuring Module and Insulin Pump Combination," the disclosure of each of which is incorporated by reference herein in its entirety. Medication delivery devices which may be provided with analyte measurement system as described herein include, e.g., a needle, syringe, pump, catheter, inhaler, transdermal patch, or combination thereof. In some embodiments, the medication delivery device or system may be in the form of a drug delivery injection pen such as a pen-type injection device incorporated within the housing of an analyte measurement system. Additional information is provided in U.S. Pat. Nos. 5,536,249 and 5,925,021, the disclosures of each of which are incorporated by reference herein in their entirety.

The embodiments presented herein provide further advantages such as: the ability to upgrade strip port modules as new test strip technologies evolve; the ability to clean or sterilize a strip port module; and the ability to allow users to replace strip port modules without returning the entire measurement system to the manufacture.

Certain embodiments relate to in vivo (e.g., continuous monitoring) systems. A continuous monitoring system typically includes a sensor that is worn or placed below the skin, a transmitter that collects glucose information from the sensor, and a receiver that collects the information from the transmitter. The sensor can collect glucose level information continuously, periodically, or at other intervals. Advantageously, a user is relieved from having to repeatedly lance his or her body to collect a blood sample once the sensor is inserted, although the sensor (e.g., an electrochemical sensor that is inserted into a body) can be replaced. U.S. Pat. No. 6,175,752, which is hereby incorporated by reference in its entirety, discloses additional examples of a continuous monitoring system.

Embodiments of the invention relate to components of a continuous monitoring system that may be replaceable. In one embodiment, the interface between the sensor and the transmitter may become contaminated. The transmitter or sensor control unit, for example, may have an interface with the sensor that has been molded to form a barrier between the transmitter's contacts and circuitry internal to the transmitter. This allows the transmitter's contacts to be washed without damaging the transmitter's circuitry. Alternatively, the contacts may be included in a replaceable port that can be replaced as needed. Similarly, the interface on the sensor may be molded to form a barrier to contamination or be replaceable.

Embodiments of the invention further extend to kits. Examples of a kit include a measurement device with one or more strip connectors. In some kits, different strip connectors or ports for different types of strips may be included. This allows the measurement device to be used with different strip form factors. The kits may also include a plurality of test strips. In certain examples, the measurement device may be configured for use with disposable test strips as well as with test strips that are configured for continuous monitoring systems. Thus, the measurement device may include a receiver to receive information from a transmitter that collects glucose information from an inserted sensor. The measurement device may also include a strip connector, such as those disclosed herein, for use with single use test strips.

Analyte Test Strips

Analyte test strips for use with the present devices can be of any kind, size, or shape known to those skilled in the art; for example, FREESTYLE® and FREESTYLE LITE™ test strips, as well as PRECISION™ test strips sold by ABBOTT DIABETES CARE Inc. In addition to the embodiments specifically disclosed herein, the devices of the present disclosure can be configured to work with a wide variety of analyte test strips, e.g., those disclosed in U.S. patent application Ser. No. 11/461,725, filed Aug. 1, 2006, now U.S. Pat. No. 7,866,026; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, now U.S. Pat. No. 8,262,874, and U.S. Patent Application Publication No. 2009/0095625; U.S. Pat. Nos. 6,616,819; 6,143,164; 6,592,745; 6,071,391 and 6,893,545; the disclosures of each of which are incorporated by reference herein in their entirety.

Calculation of Medication Dosage

In one embodiment, the analyte measurement system may be configured to measure the blood glucose concentration of a patient and include instructions for a long-acting insulin dosage calculation function. Periodic injection or administration of long-acting insulin may be used to maintain a baseline blood glucose concentration in a patient with Type-1 or Type-2 diabetes. In one aspect, the long-acting medication dosage calculation function may include an algorithm or routine based on the current blood glucose concentration of a diabetic patient, to compare the current measured blood glucose concentration value to a predetermined threshold or an individually tailored threshold as determined by a doctor or other treating professional to determine the appropriate dosage level for maintaining the baseline glucose level. In one embodiment, the long-acting insulin dosage calculation function may be based upon LANTUS® insulin, available from Sanofi-Aventis, also known as insulin glargine. LANTUS® is a long-acting insulin that has up to a 24 hour duration of action. Further information on LANTUS® insulin is available at the website located by placing "www" immediately in front of ".lantus.com". Other types of long-acting insulin include Levemir® insulin available from NovoNordisk (further information is available at the website located by placing "www" immediately in front of ".levemir-us.com". Examples of such embodiments are described in U.S. Patent Application Publication No. 2010/01981142, the disclosure of which is incorporated herein by reference in its entirety.

Strip Port Configured to Receive Test Strips for Different Analytes

In another embodiment, there is provided an analyte measurement system for multi-chemistry testing. The test strips are for chemical analysis of a sample, and are adapted for use in combination with a measuring device having a test port and capable of performing a multiplicity of testing functionalities. Each type of test strip corresponds to at least one of the testing functionalities, and at least some types of test strips have indicators of the testing functionality on them. The test port is adapted for use in combination with a multiplicity of different types of test strips and includes a sensor capable of specifically interacting with the indicator(s) on the test strips, thereby selecting at least one of the multiplicity of testing functionalities corresponding to the type of test strip. Such system would include a strip port that can be used to read a test strip for glucose and a test strip for ketone bodies. Examples of such embodiment are provided in U.S. Pat. No. 6,773,671, which is incorporated herein by reference in its entirety.

Strip Port Configured to Receive Test Strips Having Different Dimensions and/or Electrode Configurations In some embodiments, an analyte measurement system as described herein includes a strip port configured to receive test strips having different dimensions and/or electrode configurations, e.g., as described in the U.S. patent application Ser. No. 12/695,947 filed on Jan. 28, 2010, now U.S. Pat. No. 8,828,330, and entitled "Universal Test Strip Port", the disclosure of which is incorporated by reference herein in its entirety.

Implanted Analyte Sensor

In some embodiments, an analyte measurement system as described herein may include an implanted or partially implanted analyte sensor, e.g., a system including an implanted or partially implanted glucose sensor (e.g., a continuous glucose sensor). A system including an implanted or partially implanted glucose sensor may include an analyte measurement system as described herein, which is configured to receive analyte data from the implanted or partially implanted glucose sensor either directly or through an intermediate device, e.g., an RF-powered measurement circuit coupled to an implanted or partially implanted analyte sensor. In some embodiments, where an analyte measurement system according to the present disclosure is integrated with an implanted sensor, the analyte measurement system does not include a strip port for receiving an analyte test strip. In one embodiment, the analyte measurement system may be used to calibrate the analyte monitoring system, e.g., using one point calibration or other calibration protocol. For additional information, see U.S. Pat. No. 6,175,752, the disclosure of which is incorporated by reference herein in its entirety. In some embodiments, the analyte measurement system may be configured to communicate with the implanted or partially implanted analyte sensor via Radio Frequency Identification (RFID) and provide for intermittent or periodic interrogation of the implanted analyte sensor.

Exemplary analyte monitoring systems that may be utilized in connection with the disclosed analyte measurement system include those described in U.S. Pat. Nos. 7,041,468; 5,356,786; 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; 5,264,014; 5,262,305; 5,320,715; 5,593,852; 6,746,582; 6,284,478; 7,299,082; U.S. Provisional Application No. 61/149,639, entitled "Compact On-Body Physiological Monitoring Device and Methods Thereof", U.S. patent application Ser. No. 11/461,725, filed Aug. 1, 2006, now U.S. Pat. No. 7,866,026, entitled "Analyte Sensors and Methods"; U.S. patent application Ser. No. 12/495,709, filed Jun. 30, 2009, now U.S. Patent Application Publication No. 2010/0326842, entitled "Extruded Electrode Structures and Methods of Using Same"; U.S. Patent Application Publication No. 2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; US Patent Application Publication No. 2010/0198034; and U.S. Provisional Application No. 61/149,639 titled "Compact On-Body Physiological Monitoring Device and Methods Thereof", the disclosures of each of which are incorporated herein by reference in their entirety.

Communication Interface

As discussed previously herein, an analyte measurement system according to the present disclosure can be configured to include a communication interface. In some embodiments, the communication interface includes a receiver and/or transmitter for communicating with a network and/or another device, e.g., a medication delivery device and/or a patient monitoring device, e.g., a continuous glucose monitoring device. In some embodiments, the communication interface is configured for communication with a health management system, such as the CoPilot™ system available from Abbott Diabetes Care Inc., Alameda, Calif.

The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the analyte measurement system and other external devices such as a computer terminal (for example, at a physician's office or in hospital environment), an external medical device, such as an infusion device or including an insulin delivery device, or other devices that are configured for similar complementary data communication.

In one embodiment, the communication interface is configured for infrared communication, Bluetooth® communication, or any other suitable wireless communication protocol to enable the analyte measurement system to communicate with other devices such as infusion devices, analyte monitoring devices, computer terminals and/or networks, communication enabled mobile telephones, personal digital assistants, or any other communication devices which the patient or user of the analyte measurement system may use in conjunction therewith, in managing the treatment of a health condition, such as diabetes.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the analyte measurement system is configured to wirelessly communicate with a server device via the communication interface, e.g., using a common standard such as 802.11 or Bluetooth® RF protocol, or an IrDA infrared protocol. The server device could be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen. With such an arrangement, the user can control the analyte measurement system indirectly by interacting with the user interface(s) of the server device, which in turn interacts with the analyte measurement system across a wireless link.

In some embodiments, the communication interface is configured to automatically or semi-automatically communicate data stored in the analyte measurement system, e.g., in an optional data storage unit, with a network or server device using one or more of the communication protocols and/or mechanisms described above.

Input Unit

As discussed previously herein, an analyte measurement system according to the present disclosure can be configured to include an input unit and/or input buttons coupled to the housing of the analyte measurement system and in communication with a controller unit and/or processor. In some embodiments, the input unit includes one or more input buttons and/or keys, wherein each input button and/or key is designated for a specific task. Alternatively, or in addition, the input unit may include one or more input buttons and/or keys that can be 'soft buttons' or 'soft keys'. In the case where one or more of the input buttons and/or keys are 'soft buttons' or 'soft keys', these buttons and/or keys may be used for a variety of functions. The variety of functions may be determined based on the current mode of the analyte measurement system, and may be distinguishable to a user by the use of button instructions shown on an optional display unit of the analyte measurement system. Yet another input method may be a touch-sensitive display unit, as described in greater detail below.

In addition, in some embodiments, the input unit is configured such that a user can operate the input unit to adjust time and/or date information, as well as other features or settings associated with the operation of an analyte measurement system.

Display Unit

As discussed previously herein, in some embodiments, an analyte measurement system according to the present disclosure includes an optional display unit or a port for coupling an optional display unit to the analyte measurement system. The display unit is in communication with a control unit and/or processor and displays the analyte test strip signals and/or results determined from the analyte test strip signals including, for example, analyte concentration, rate of change of analyte concentration, and/or the exceeding of a threshold analyte concentration (indicating, for example, hypo- or hyperglycemia).

The display unit can be a dot-matrix display, e.g., a dot-matrix LCD display. In some embodiments, the display unit includes a liquid-crystal display (LCD), thin film transistor liquid crystal display (TFT-LCD), plasma display, light-emitting diode (LED) display, seven-segment display, E-ink (electronic paper) display or combination of two or more of the above. The display unit can be configured to provide, an alphanumeric display, a graphical display, a video display, an audio display, a vibratory output, or combinations thereof. The display can be a color display. In some embodiments, the display is a backlit display.

The display unit can also be configured to provide, for example, information related to a patient's current analyte concentration as well as predictive analyte concentrations, such as trending information.

In some embodiments an input unit and a display unit are integrated into a single unit, for example, the display unit can be configured as a touch sensitive display, e.g., a touch-screen display, where the user may enter information or commands via the display area using, for example, the user's finger, a stylus or any other suitable implement, and where, the touch sensitive display is configured as the user interface in an icon driven environment, for example.

In some embodiments, the display unit does not include a screen designed to display results visually. Instead, in some embodiments the optional display unit is configured to communicate results audibly to a user of the analyte measurement system, e.g., via an integrated speaker, or via separate speakers through a headphone jack or Bluetooth® headset.

Expanding Menu Item for Improved Readability

In some embodiments, the display unit includes a graphical user interface including a plurality of menu items, wherein the display unit is configured to provide clarification with respect to the meaning of a menu item based on a user's response speed with respect to a user input for the menu item. The menu item could take any of a variety of forms, e.g., text, icon, object or combination thereof.

In one embodiment, the graphical user interface includes a menu which in turn includes a plurality of selectable menu items. As a user navigates through the menu, e.g., by highlighting or scrolling through individual menu items, a menu item that is either unreadable or incomprehensible to the user could cause the user to pause over a menu item to be selected. In one embodiment, a choice can be presented to the user, e.g., using a dedicated physical button on an input unit, or a soft key on the menu, that offers further explanation of the item to be selected without actually selecting the item. For example, the graphical user interface can be configured such that after a pre-determined period of time a soft key offers an explanation of the menu item to be selected, e.g., by displaying a soft key with the word "MORE", "ADDITIONAL INFORMATION", "EXPAND", "MAGNIFY", "HELP" or a variation thereof displayed thereon.

The pre-determined period of time may be based on a fixed factory preset value, a value set by the user or a health care provider, or through an adaptive mechanism based on an analysis of the user's speed of navigation from past interactions with the graphical user interface. In one embodiment, the pre-determined period of time is from about 5 to about 20 seconds, e.g., from about 10 to about 15 seconds.

If the offer for clarification and/or additional information is selected, e.g., by pressing the softkey, then the menu item to be selected can be displayed in a "high emphasis" mode, e.g., where the item is displayed as if a magnifying lens is held on top of the selected item. In some embodiments, additional emphasis of the menu item to be selected can be provided, e.g., by making the menu item change color, blink, or increase in size to a pre-determined maximum limit.

Support for On-Demand Analyte Determination Using an Analyte Sensor

In some embodiments, an analyte measurement system according to the present disclosure is further configured to receive analyte concentration data and/or signals indicative of an analyte concentration from an analyte sensor, e.g., an implanted or partially implanted analyte sensor or a radio-frequency (RF)-powered measurement circuit coupled to an implanted or partially implanted analyte sensor. In some embodiments, the analyte sensor is a self-powered analyte sensor. An analyte measurement system according to the present disclosure may include software configured to analyze signals received from the analyte sensor. Additional information related to self-powered analyte sensors and methods of communicating therewith are provided in U.S. Patent Application Publication No. 2010/0213057, the disclosure of which is incorporated by reference herein in its entirety.

Analytes

A variety of analytes can be detected and quantified using the disclosed analyte measurement system. Analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. Nos. 6,281,006 and 6,638,716, the disclosures of each of which are incorporated by reference herein in their entirety.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

The detailed description of the figures refers to the accompanying drawings that illustrate an exemplary embodiment of an analyte measurement system. Other embodiments are possible. Modifications may be made to the embodiment described herein without departing from the spirit and scope of the present invention. Therefore, the following detailed description is not meant to be limiting.

Certain embodiments presented herein relate to electrical interfaces in measurement devices. Measurement devices often have electrical interfaces that allow them to electrically connect with another device or apparatus and perform an analysis of an analyte. A device that measures blood glucose levels, for example, includes electrical interfaces that allow the device to measure the blood glucose level from a small blood sample.

What is claimed is:

1. A diabetes management system, comprising:
a plurality of analyte measurement devices; and
a centralized server configured for data communication with the plurality of analyte measurement devices;
wherein each of the plurality of analyte measurement devices comprises:
a diabetes management software application; and
one or more processors coupled to a memory, the memory being configured to store instructions that, when executed by the one or more processors, cause the one or more processors to transmit one or more communications to the centralized server, the one or more communications comprising:
a version number associated with the diabetes management software application,
a unique patient ID associated with a user of the analyte measurement device,
data indicative of measured analyte levels associated with the user of the analyte measurement device, and
one or more timestamps associated with the data indicative of measured analyte levels, and
wherein the centralized server includes at least one computer readable medium having instructions executable by at least one processing device that, when executed, cause the at least one processing device to:
store the unique patient ID received from each of the plurality of analyte measurement devices in a database, and
aggregate, based on the stored unique patient ID, the data indicative of measured analyte levels from each of the plurality of analyte measurement devices.

2. The system of claim 1, wherein at least one of the plurality of analyte measurement devices includes a communication module adapted for wireless communication with the centralized server.

3. The system of claim 2, wherein the communication module is configured to wirelessly communicate with the centralized server according to a 802.11 communication protocol.

4. The system of claim 2, wherein the communication module is configured to communicate with the centralized server according to a cellular communication protocol.

5. The system of claim 2, wherein at least one of the plurality of analyte measurement devices comprises a smartphone.

6. The system of claim 1, wherein the instructions of the at least one computer readable medium of the centralized server, when executed by the at least one processing device, further cause the at least one processing device to aggregate the data indicative of measured analyte levels from each of the plurality of analyte measurement devices based, at least in part, on a key code associated with the diabetes management software application.

7. The system of claim 1, wherein the instructions of the at least one computer readable medium of the centralized server, when executed by the at least one processing device, further cause the at least one processing device to provide an indication that the version number of the diabetes management software application is valid, and wherein the version number of the diabetes management software application is indicative of each specific version of an application installed on each analyte measurement device of the plurality of analyte measurement devices.

8. The system of claim 1, wherein at least one of the analyte measurement devices is configured to measure a blood glucose level of a patient.

9. The system of claim 1, wherein at least one of the plurality of analyte measurement devices is configured to communicate analyte measurement data to the centralized server using a wired connection.

10. The system of claim 9, wherein the wired connection is a USB connection to a personal computer, wherein the personal computer is configured for data communication with the centralized server.

11. The system of claim 1, further comprising a plurality of transmitters, each of which is operatively coupled with a corresponding sensor, wherein each corresponding sensor comprises a portion that is placed below a user's skin and configured to sense an analyte level, wherein each transmitter is configured to collect signals indicative of the analyte level from the corresponding sensor, and wherein the plurality of analyte measurement devices is configured to collect analyte level information from the plurality of transmitters.

12. The system of claim 11, wherein each of the plurality of analyte measurement devices is configured to communicate with a corresponding transmitter of the plurality of transmitters according to a Bluetooth communication protocol.

13. An analyte monitoring system, comprising:

(1) an on-body unit comprising:

a sensor, at least a portion of which is placed below a user's skin and configured to sense glucose levels of the user, and a communication module operatively coupled to the sensor and configured to transmit data indicative of the glucose levels; and (2) a hand-held receiver comprising:

one or more communication modules configured for:

wireless communication with the on-body unit and to receive the data indicative of the glucose levels, and data communication with a centralized server, a diabetes management software application, and one or more processors coupled to a memory, the memory being configured to store instructions that, when executed by the one or more processors, cause the one or more processors to transmit one or more communications to the centralized server, the one or more communications comprising:

a version number associated with the diabetes management software application;

a unique patient ID associated with the user of the analyte monitoring system;

the data indicative of the glucose levels; and one or more timestamps associated with the data indicative of the glucose levels; and (3) the centralized server configured for data communication with the hand-held receiver, wherein the centralized server includes at least one computer readable medium having instructions executable by at least one processing device that, when executed, cause the at least one processing device to:

store the unique patient ID received from the hand-held receiver in a database, and aggregate, based on the stored unique patient ID, the data indicative of the glucose levels from the hand-held receiver.

14. The system of claim 13, wherein the one or more communication modules of the hand-held receiver is configured to communicate with the communication module of the on-body unit according to a Bluetooth communication protocol.

15. The system of claim 14, wherein the one or more communication modules of the hand-held receiver is configured to communicate with the centralized server according to a 802.11 communication protocol.

16. The system of claim 14, wherein the one or more communication modules of the hand-held receiver is configured to communicate with the centralized server according to a cellular communication protocol.

17. The system of claim 14, wherein the hand-held receiver comprises a smartphone.

18. The system of claim 13, wherein the data indicative of the glucose levels is aggregated by the centralized server based, at least in part, on the key code associated with the diabetes management software application.

19. The system of claim 13, wherein the hand-held receiver is configured to receive an indication of whether the diabetes management software is valid based, at least in part, on the version number associated with the diabetes management software application, and wherein the version number associated with the diabetes management software application is indicative of a specific version of an application installed on the hand-held receiver.

* * * * *